US00PP15610P2

(12) United States Plant Patent
Hanes

(10) Patent No.: US PP15,610 P2
(45) Date of Patent: Mar. 1, 2005

(54) ***VERBENA* PLANT NAMED 'LAN ROYPUREYE'**

(50) Latin Name: *Verbena hybrida*
Varietal Denomination: Lan Roypureye

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 10/818,503

(22) Filed: Apr. 5, 2004

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of *Verbena* plant named 'Lan Roypureye', characterized by its compact, low and outwardly spreading, and decumbent plant habit; freely branching habit; early and uniform flowering habit and dark purple-colored flowers with distinct white-colored centers.

1 Drawing Sheet

Botanical classification/cultivar designation: *Verbena hybrida* cultivar Lan Roypureye.

BACKGROUND OF THE INVENTION

The present Invention relates to a new and distinct cultivar of *Verbena* plant, botanically known as *Verbena hybrida,* and hereinafter referred to by the name 'Lan Roypureye'.

The new *Verbena* is a product of a planned breeding program conducted by the Inventor in Gilroy, Calif. The objective of the breeding program is to develop new compact *Verbena* cultivars with early and uniform flowering, good basal branching, attractive flower and foliage coloration, and tolerance to Powdery Mildew.

The new *Verbena* originated from a cross-pollination made by the Inventor in May, 2000 of a proprietary *Verbena hybrida* selection identified as code number 99-980-2, not patented, as the female, or seed, parent with a proprietary *Verbena hybrida* selection identified as code number 99-978-1, not patented, as the male, or pollen, parent. The cultivar Lan Roypureye was discovered and selected by the Inventor as a flowering plant within the progeny from this cross-pollination in a controlled environment in Gilroy, Calif. in January, 2001.

Asexual reproduction of the new cultivar by terminal cuttings in Gilroy, Calif., since January, 2001 has shown that the unique features of this new *Verbena* are stable and reproduced true to type in successive generations of asexual reproduction.

SUMMARY OF THE INVENTION

The following traits have been repeatedly observed and are determined to be the unique characteristics of 'Lan Roypureye'. These characteristics in combination distinguish 'Lan Roypureye' as a new and distinct cultivar:

1. Compact, low and outwardly spreading, and decumbent plant habit.
2. Freely branching habit.
3. Early and uniform flowering habit.
4. Dark purple-colored flowers with distinct white-colored centers.
5. Relatively less susceptible to Powdery Mildew.

In side-by-side comparisons conducted in Gilroy, Calif., plants of the new *Verbena* differed from plants of the female parent selection in the following characteristics:

1. Plants of the new *Verbena* were more compact and upright than plants of the female parent selection.
2. Flowers of plants of the new *Verbena* had distinct white-colored centers whereas flowers of plants of the female parent selection did not have distinct white-colored centers.

In side-by-side comparisons conducted in Gilroy, Calif., plants of the new *Verbena* differed from plants of the male parent selection in the following characteristics:

1. Plants of the new *Verbena* were more vigorous than plants of the male parent selection.
2. Flowers of plants of the new *Verbena* were darker purple in color than flowers of plants of the male parent selection.

Plants of the new *Verbena* can be compared to plants of the cultivar Lan Depur, disclosed in a U.S. Plant patent application No. 10/818,496. In side-by-side comparisons conducted in Gilroy, Calif., plants of the new *Verbena* differed from plants of the cultivar Lan Depur primarily in flower color as plants of the new *Verbena* had more distinct white-colored centers than plants of the cultivar Lan Depur.

The new *Verbena* can be compared to the cultivar, USBENAL25, disclosed in U.S. Plant patent application Ser. No. 10/638,688. However, in side-by-side comparisons conducted in Gilroy, Calif., plants of the new *Verbena* differed from plants of the cultivar USBENAL25 in the following characteristics:

1. Plants of the new *Verbena* were more vigorous than plants of the cultivar USBENAL25.
2. Leaves of plants of the new *Verbena* were lighter green in color than leaves of plants of the cultivar USBENAL25.
3. Flowers of plants of the new *Verbena* were fuller and more rounded than flowers than plants of the cultivar USBENAL25.
4. Flowers of plants of the new *Verbena* had distinct white-colored centers whereas flowers of plants of the cultivar USBENAL25 did not have distinct white-colored centers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Lan Roypureye'.

The photograph at the bottom of the sheet is a close-up view of typical flowers racemes and leaves of 'Lan Roypureye'.

Flower and foliage colors in the photographs may differ slightly from the color values cited in the detailed botanical description which accurately describe the colors of the new *Verbena*.

DETAILED BOTANICAL DESCRIPTION

Plants of the cultivar Lan Roypureye have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a polyethylene-covered greenhouse during the summer with day temperatures about 24 to 32° C., night temperatures about 13 to 18° C. and light levels about 2,000 foot-candles. Plants used for the photographs and description were about twelve weeks from planting rooted cuttings and were pinched twice. In the following description, color references are made to The Royal Horticultural Society Colour Chart, 1995 Edition, except where general terms of ordinary dictionary significance are used.

Botanical classification: *Verbena hybrida* cultivar Lan Roypureye.

Parentage:

*Female, or seed, parent.*—Proprietary *Verbena hybrida* selection identified as code number 99-980-2, not patented.

*Male, or pollen, parent.*—Proprietary *Verbena hybrida* selection identified as code number 99-978-1, not patented.

Propagation:

*Type cutting.*—Terminal cuttings.

*Time to initiate roots.*—About 7 to 10 days at 22 to 24° C.

*Time to produce a rooted cutting or liner.*—About three to four weeks at 22 to 24° C.

*Root description.*—Fine, fibrous; white in color.

*Rooting habit.*—Freely branching.

Plant description:

*Form.*—Compact, low and outwardly spreading, and decumbent plant habit.

*Growth and branching habit.*—Vigorous and freely-branching with about twelve main stems and multiple secondary lateral branches.

*Plant height.*—About 14 cm.

*Plant diameter or spread.*—About 69 cm.

*Lateral branches.*—Length: About 48 cm. Diameter: About 2.5 mm. Internode length: Vegetative branches, about 2 cm; reproductive branches, about 4 cm. Strength: Strong. Texture: Pubescent. Color: 146A.

*Foliage description.*—Arrangement: Opposite, simple. Length: About 3.8 cm. Width: About 3.5 cm. Shape: Deltoid. Apex: Broadly acute. Base: Attenuate. Margin: Broadly crenate. Texture, upper and lower surfaces: Slightly coarse, pubescent. Venation pattern: Pinnate, netted. Color: Developing foliage, upper surface: 146A. Developing foliage, lower surface: 147B. Fully expanded foliage, upper surface: 147A. Fully expanded foliage, lower surface: 147B. Venation, upper and lower surfaces: 147C. Petiole: Length: About 6 mm. Diameter: About 2 mm. Color: 147C.

Flower description:

*Flower type and habit.*—Single upright salverform flowers arranged on terminal racemes; flowers sessile. Freely flowering with about 22 flowers per raceme; about three racemes per lateral branch. Inflorescences positioned above and beyond the foliage. Flowers last about five to seven days under greenhouse conditions. Flowers not persistent.

*Fragrance.*—None detected.

*Flowering season.*—In the garden, flowering is continuous from spring until fall.

*Inflorescence size.*—Height: About 3.3 cm. Diameter: About 6.5 cm.

*Flower size.*—Diameter: About 2.2 cm. Tube length: About 2.8 cm.

*Flowers buds.*—Length: About 1.3 cm. Diameter: About 3 mm. Shape: Tubular. Color: 79A.

*Petals.*—Quantity/arrangement: Five per flower fused at base. Lobe length: About 1 cm. Lobe width: About 9 mm. Shape: Cordate. Apex: Emarginate. Margin: Entire. Texture, upper and lower surfaces: Velvety, smooth. Color: When opening, upper surface: Brighter than 79A. When opening, lower surface: 83B. Fully opened, upper surface: Brighter than 49A; towards the center, close to 155A. With development, towards the apex, closer to 83A. Fully opened, lower surface: 83C. Throat: Close to 150C.

*Sepals.*—Quantity/arrangement: Five, fused into a tube. Length: About 1.1 cm. Diameter: Less than 1 mm. Shape: Ligulate. Apex: Acuminate. Margin: Entire. Texture, upper and lower surfaces: Coarse, pubescent. Color, upper surface: 147B. Color, lower surface: 147C.

*Peduncles.*—Length: About 8.5 cm. Diameter: About 1.5 mm. Angle: Upright or curving upward on horizontal stems. Strength: Strong. Color: 146A.

*Reproductive organs.*—Stamens: Quantity: Four. Anther shape: Ovoid. Anther length: Less than 1 mm. Anther color: 150A. Pollen amount: Scarce. Pollen color: 1A. Pistils: Quantity: One. Pistil length: About 2 cm. Stigma shape: Bi-parted. Stigma color: 145A. Style length: About 1.8 cm. Style color: 146D. Ovary color: 145A.

*Fruit/seed.*—Fruit and seed production has not been observed.

Disease/pest resistance: Plants of the new *Verbena* have been observed to be relatively less susceptible to Powdery Mildew. Plants of the new *Verbena* have not been observed to be resistant to other pathogens and pests common to *Verbena*.

Temperature tolerance: Plants of the new *Verbena* have been observed to be tolerant to temperatures ranging from 2 to 40° C.

It is claimed:

1. A new and distinct cultivar of *Verbena* plant named 'Lan Roypureye', as illustrated and described.

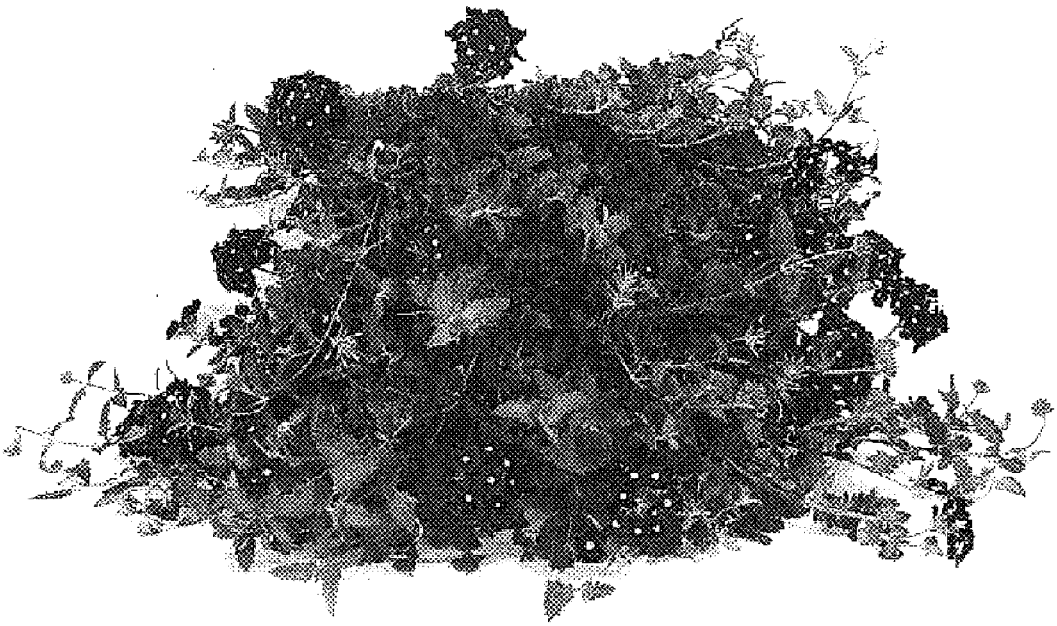
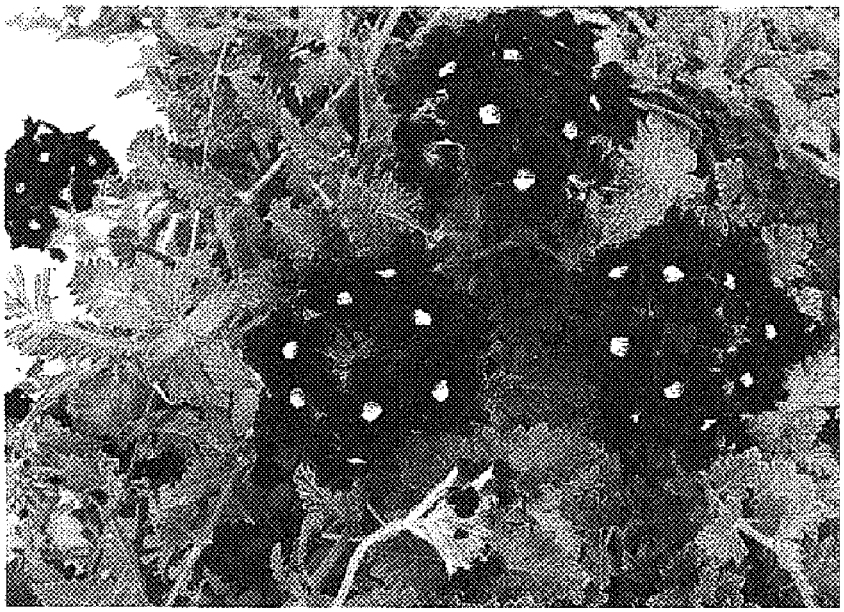

* * * * *